July 25, 1961 W. LEE Plant Pat. 2,075
BOUGAINVILLEA PLANT
Filed April 8, 1960
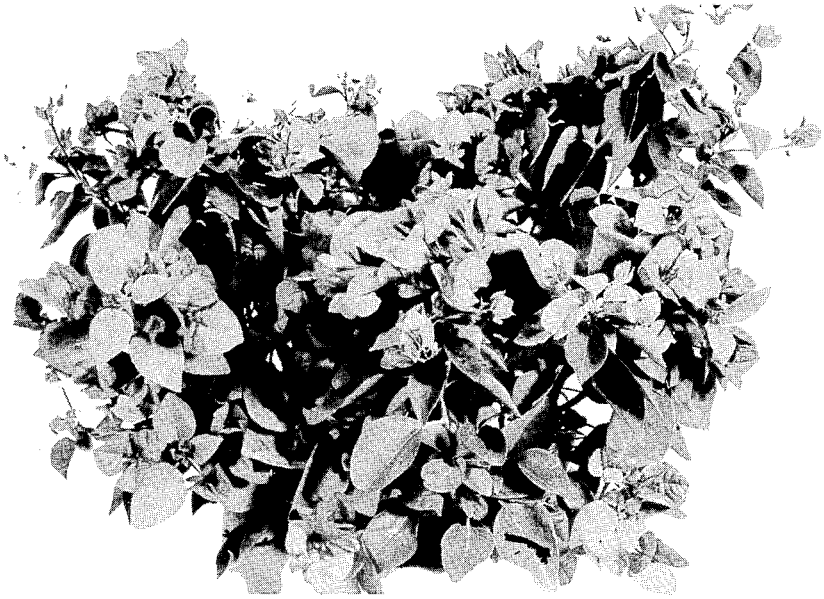
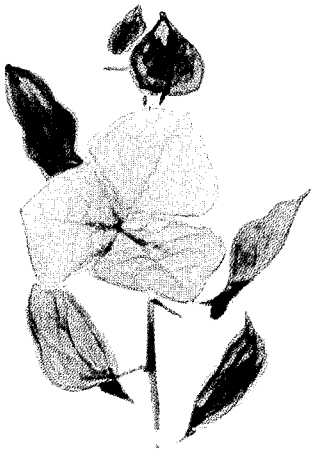
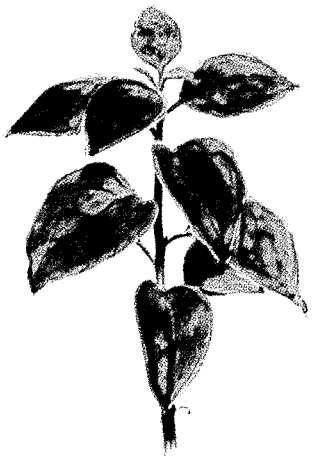
INVENTOR
WALTER LEE
BY J. F. Cuneo
ATTORNEY United States Patent Office Plant Pat. 2,075
Patented July 25, 1961

2,075

BOUGAINVILLEA PLANT

Walter Lee, Bellflower, Calif., assignor to Monrovia Nursery Co., Azusa, Calif., a corporation of California Filed Apr. 8, 1960, Ser. No. 21,075
1 Claim. (Cl. 47—60)

The present discovery relates to a new and distinct variety of bougainvillea plant which is of the bush variety.

The discovery of this new species or variety was made by me in July of 1954, on my property located at 9429 East Linden Avenue, Bellflower, County of Los Angeles, State of California, as a sport. This sport was a branch growing from the parent plant which was a sepcimen of bougainvillea plant popularly designated as "Temple Fire," a non-patented variety. To the best of my knowledge and belief the new species is not a form of *Bougainvillea glabra.*

After the discovery of the new variety cuttings were made and numerous generations of the plant have been propagated asexually at Bellflower, California. Thousands of cuttings have been made and all descendants exhibit the distinguishing characteristic of the new and distinct variety, thereby establishing that the strain is true. The plant cannot be reproduced true from seed.

The new and distinct variety of bougainvillea plant is characterized as to novelty by its compact bushy growth habit; its abundance of iridescent crimson bracts and flowers, and its longer flowering period. The new variety differs from its parent plant in that the bracts and flowers have a bright iridescent crimson color that is distinctly different from the dull red color of the bracts of the parent plant. The number of flowers and bracts are more numerous and the plant bears the colorful bracts for a much longer period of time than those borne by the parent species; the blooming period of the new variety extends substantially from March through December in southern California. As its parent plant this species of bougainvillea is a bush whereas the majority of bougainvilleas are of the vine type.

The new variety of bougainvillea plant is shown in the accompanying drawings. The black and white photograph at the top of the drawing shows a side view of a plant in a container and clearly illustrates its bushy growth. The colored illustration at the left shows a branch with leaves, bracts, flowers and spines while the colored view on the right includes a branch with leaves showing their normal arrangment. The bracts have a definite iridescence and in the drawing an effort has been made to indicate this iridescence, however, this effect is extremely difficult to reproduce in either oil or water colors.

A detailed description of the new and distinct variety follows and to facilitate identification of the important colors, the terminology adopted by the British Horticultural Color Charts is followed.

*The flower*

Flowers: The true flowers of the bougainvillea plant are small, inconspicuous and tubular. The margin of the flower has usually from five to six lobes. The so-called flower of the bougainvillea consists of the true flowers and the accompanying bracts. These appear as a group of three flowers and three bracts attached to a stem.

Flowers borne: The groups of flowers and bracts are borne in panicles of from two, three or more groups.

Number of blooms: The plant produces an abundant number of bracts and flowers.

Blooming period: The normal blooming period usually begins in March and continues through December.

Shape of bracts: The shape of the bracts is cordate-ovate. The bracts exhibit prominent central veins with the side veins less pronounced.

Color: The bracts and flowers exhibit a color, when first opened, that is best identified as Indian Lake 826/3 and have a pronounced iridescence, which, as previously stated is very difficult to reproduce with either oil or water colors. When the mature bracts are ready to fall off the plant they fade to a color that is best identified as Solferino Purple 26/1.

*The plant*

Growth habit: The natural habit of growth of the plant is a moderately dense, compact shrub.

Size: The height of the plant at the end of six years growth is from two and one half to three feet, and the plant has an overall spread of four feet or slightly more.

Foliage:

*Leaves.*—The leaves are alternate, and are abundant in quantity.

*Shape.*—Leaves are ovate-acuminate, entire, with the base of the leaves being acute.

*Size.*—Leaves vary in width from one and a quarter to one and a half inches in width, and are between two and two and one half inches long.

*Petiole.*—Petioles average five eighths of an inch in length.

*Color.*—The upper side of a mature leaf is Spinach Green 0960. The underside of the mature leaf is Spinach Green 0960/2.

Spines: There are occasional spines that are substantially straight and needle-like and appear at the axial of the leaves. Size—the spines vary from one quarter of an inch to nine sixteenths of an inch in length.

Branches:

*New growth.*—New branch growth is light green and is moderately pubescent.

*Mature growth.*—Mature branches have a rough, beige colored bark.

Having thus described my invention, I claim:

A new and distinct variety of bougainvillea plant characterized as to novelty by the iridescent crimson red color of its bracts and flowers, its longer flowering period, and its compact bushy growth, substantially as shown and described.

No references cited.